US009403150B2

(12) United States Patent
Lu et al.

(10) Patent No.: US 9,403,150 B2
(45) Date of Patent: Aug. 2, 2016

(54) METAL CATALYST COMPOSITION

(75) Inventors: Junling Lu, Downers Grove, IL (US);
Peter Stair, Northbrook, IL (US);
Baosong Fu, Nanjing (CN); Harold H. Kung, Wilmette, IL (US); Mayfair C Kung, Wilmette, IL (US)

(73) Assignee: Northwestern University, Evanston, IL (US)

( * ) Notice: Subject to any disclaimer, the term of this patent is extended or adjusted under 35 U.S.C. 154(b) by 178 days.

(21) Appl. No.: 14/119,475

(22) PCT Filed: May 24, 2012

(86) PCT No.: PCT/US2012/039343
§ 371 (c)(1),
(2), (4) Date: Nov. 22, 2013

(87) PCT Pub. No.: WO2012/166514
PCT Pub. Date: Dec. 6, 2012

(65) Prior Publication Data
US 2014/0094635 A1    Apr. 3, 2014

Related U.S. Application Data

(60) Provisional application No. 61/520,085, filed on Jun. 3, 2011.

(51) Int. Cl.
*B01J 12/00* (2006.01)
*B01J 37/08* (2006.01)
(Continued)

(52) U.S. Cl.
CPC  *B01J 23/44* (2013.01); *B01J 21/04* (2013.01); *B01J 23/38* (2013.01); *B01J 35/002* (2013.01);
(Continued)

(58) Field of Classification Search
CPC .......... B01J 12/00; B01J 12/007; B01J 21/04; B01J 37/0225; B01J 37/0228; B01J 37/024; B01J 37/0244; B01J 37/08; B01J 37/14; B01J 35/10; C23C 16/40; C23C 16/403; C23C 16/45525
USPC ................................ 502/300, 355; 427/248.1
See application file for complete search history.

(56) References Cited

U.S. PATENT DOCUMENTS 8,815,766 B2 *   8/2014   Lu ............................ B01J 23/38
                                                       502/240
(Continued)

FOREIGN PATENT DOCUMENTS

WO    2010135107    11/2010
WO    2011031288     3/2011

OTHER PUBLICATIONS

"Nucleation and Growth of Noble Metals on Oxide Surfaces Using Atomic Layer Deposition," J. W. Elam et al. ECS Transactions, 3 (15), pp. 271-278 (2007).*

(Continued)

*Primary Examiner* — Patricia L Hailey
(74) *Attorney, Agent, or Firm* — Brooks, Cameron & Huebsch, PLLC (57) ABSTRACT

Embodiments include metal catalyst compositions and methods of forming metal catalyst compositions. A metal catalyst composition can be formed by (a) contacting a supported metal catalyst surface with a ligand-containing alumina precursor for a predetermined contact time to form an intermediate layer having a plurality of aluminum moieties that chemically bond to the supported metal catalyst surface, optionally, contacting the intermediate layer of aluminum moieties with an inert gas for a predetermined intermediate stripping time to remove unreacted ligand-containing alumina precursors, (b) reacting the aluminum moieties with an oxidation reagent for a predetermined reaction time to convert at least a portion of the ligands to hydroxyl groups thereby forming a layer of the alumina over-coat on the supported metal catalyst surface or a previously formed layer of the alumina over-coat, (c) contacting the layer of the alumina over-coat formed in step (b) with an inert gas for a predetermined stripping time to remove unreacted oxidation reagents, replicating the sequential steps (a-c) to form an additional layer of the alumina over-coat, and (d) activating the alumina over-coat, after forming a final layer of the alumina over-coat, to form a plurality of pores therein.

11 Claims, 10 Drawing Sheets

(51) Int. Cl.
*B01J 37/14* (2006.01)
*B01J 35/10* (2006.01)
*B01J 23/44* (2006.01)
*B01J 21/04* (2006.01)
*B01J 23/38* (2006.01)
*B01J 35/00* (2006.01)
*B01J 37/02* (2006.01)
*C23C 16/30* (2006.01)
*C23C 16/455* (2006.01)
*C07C 5/333* (2006.01)
*C07C 5/42* (2006.01)
*B01J 37/12* (2006.01)
*B01J 37/18* (2006.01)
*C07C 5/48* (2006.01)

(52) U.S. Cl.
CPC ............ *B01J 35/006* (2013.01); *B01J 35/0073* (2013.01); *B01J 35/1019* (2013.01); *B01J 35/1057* (2013.01); *B01J 35/1061* (2013.01); *B01J 37/0209* (2013.01); *B01J 37/0228* (2013.01); *B01J 37/0244* (2013.01); *B01J 37/08* (2013.01); *B01J 37/12* (2013.01); *B01J 37/14* (2013.01); *B01J 37/18* (2013.01); *C07C 5/3335* (2013.01); *C07C 5/3337* (2013.01); *C07C 5/42* (2013.01); *C07C 5/48* (2013.01); *C23C 16/30* (2013.01); *C23C 16/45531* (2013.01); *C23C 16/45555* (2013.01); *C07C 2521/04* (2013.01); *C07C 2521/06* (2013.01); *C07C 2521/08* (2013.01); *C07C 2521/18* (2013.01); *C07C 2523/02* (2013.01); *C07C 2523/06* (2013.01); *C07C 2523/10* (2013.01); *C07C 2523/20* (2013.01); *C07C 2523/36* (2013.01); *C07C 2523/42* (2013.01); *C07C 2523/44* (2013.01); *C07C 2523/46* (2013.01); *C07C 2523/50* (2013.01); *C07C 2523/52* (2013.01); *C07C 2523/72* (2013.01); *C07C 2523/745* (2013.01); *C07C 2523/755* (2013.01); *Y02P 20/52* (2015.11)

(56) References Cited

U.S. PATENT DOCUMENTS

| 2004/0203254 | A1* | 10/2004 | Conley | C23C 16/45527 438/778 |
| 2007/0065578 | A1* | 3/2007 | McDougall | C23C 16/4404 427/248.1 |
| 2007/0148347 | A1* | 6/2007 | Hatanpaa | C23C 16/40 427/248.1 |
| 2007/0281105 | A1* | 12/2007 | Mokhlesi | C23C 16/40 427/569 |
| 2009/0233790 | A1 | 9/2009 | Vajda et al. | |

OTHER PUBLICATIONS

"Oxidative dehydrogenation of ethane over alumina-supported Pd catalysts. Effect of alumina overlayer", Baosong Fu et al. Journal of Catalysis 297 (2013), pp. 289-295.*

"Nanotechnology: applications and potentials for heterogeneous catalysis," Harold H. Kung et al. Catalysis Today 97 (2004), pp. 219-224.*

International Search Report and Written Opinion from related PCT Application PCT/US2012/039343 dated Nov. 6, 2012, 16 pgs.

* cited by examiner

METAL CATALYST COMPOSITION

This application is a National Stage application under 35 U.S.C. 371 of PCT/US2012/039343, filed on May 24, 2012 and published as WO 2012/166514 on Dec. 6, 2012, which claims the benefit of U.S. Provisional Application Ser. No. 61/520,085, filed Jun. 3, 2011, the entire contents of which are incorporated herein by reference in its entirety.

This disclosure relates to metal catalyst compositions, methods of forming metal catalyst compositions, and in particular metal catalyst compositions that reduce coke formation during dehydrogenation reactions that produce olefins.

Dehydrogenation converts alkanes to alkenes (i.e., olefins) using metal catalysts, which increase the selectivity of the reaction. While metal catalysts increase the selectivity, they are vulnerable to carbon buildup, i.e., "coking." Coking deactivates the metal catalyst within minutes (e.g., 10 minutes (min)), after the dehydrogenation begins and blocks the flow of reactants, which results in higher pressure drops in the reactor.

To remove coke, the metal catalysts undergo an oxidation treatment at high temperatures (e.g, greater than 500 degrees Celsius (° C.)). This adds cost to the olefin production, reduces carbon efficiency, and leads to sintering of metal particles of the metal catalyst, which causes catalyst degradation.

"Over-coat" refers to a thin coating controlled to an atomic level that is deposited onto nano-size metal particles of a catalyst and the catalyst support.

"Alumina over-coat" refers to a coating of alumina controlled to an atomic level that is deposited onto nano-size metal particles of a catalyst and the catalyst support.

"Coking" refers to a solid carbonaceous buildup during the dehydrogenation reaction.

"Substrate" refers to a base and/or a support.

"Layer" refers to a coating. A layer can be a substrate and/or can be formed on a substrate or on another layer. A layer can be formed from the compounds of the present disclosure using an ALD process. Theoretically, an ALD cycle forms a layer that is uniformly one atom or molecule thick on an exposed surface. However, the layer may not occur on all portions of the exposed surface. Such a partial layer is understood to be a layer herein.

"Deposition", "deposition process" and "vapor deposition process" refer to a process in which a layer is formed on one or more surfaces of a substrate and/or a layer.

"Dehydrogenation" refers to a chemical reaction that involves the elimination of hydrogen ($H_2$) and can include dehydrogenation reactions that are oxidative or nonoxidative reaction.

"Atomic layer deposition" (ALD) is also meant to include the related terms "atomic layer epitaxy" (ALE), molecular beam epitaxy (MBE), gas source MBE, organometallic MBE, and chemical beam epitaxy when performed with alternating pulses of chemical components.

"As-prepared" refers to the metal catalyst composition prior to activation.

"Moieties" refers to any discrete unit of material structure, where the discrete units are comprised of atoms, molecules, ions or combinations thereof.

"Ligand" refers to refers to a nonmetallic ion, molecule, or atom that is attached to a central atom of a coordination compound.

A method of forming a metal catalyst composition includes performing a plurality of atomic layer deposition cycles to form an alumina over-coat on a supported metal catalyst, where one or more of the atomic layer deposition cycles include sequential steps: (a) contacting a supported metal catalyst surface with a ligand-containing alumina precursor for a predetermined contact time to form an intermediate layer having a plurality of aluminum moieties that chemically bond to the supported metal catalyst surface, (b) reacting the aluminum moieties with an oxidation reagent for a predetermined reaction time to convert at least a portion of the ligands to hydroxyl groups thereby forming a layer of the alumina over-coat on the supported metal catalyst surface or a previously formed layer of the alumina over-coat, (c) prior to replicating the sequential steps (a) and (b) to form an additional layer of the alumina over-coat, contacting the layer of the alumina over-coat formed in step (b) with an inert gas for a predetermined final stripping time to remove unreacted oxidation reagents, and (d) activating the alumina over-coat, after forming a final layer of the alumina over-coat, to form a plurality of pores therein. For one or more embodiments, at least 80 percent (%) of the plurality of pores have a diameter within a range of from 0.3 nanometer (nm) to 5 nm. The metal catalyst composition reduces an amount of coke formed during a dehydrogenation or an oxidative dehydrogenation reaction, as compared to same supported metal catalysts without the alumina over-coat.

The metal catalyst composition includes the supported metal catalyst having the support with the plurality of metal particles, and an alumina over-coat deposited on a surface of the supported metal catalyst by atomic layer deposition followed by activating the alumina over-coat. Activating the alumina over-coat forms pores in the alumina over-coat, at least 80 percent (%) of the plurality of pores have a diameter within a range of from 0.3 nanometer (nm) to 5 nm, and where the alumina over-coat has a thickness within a range of from 1 nm to 100 nm. The disclosed metal catalyst compositions reduce an amount of coke formed during a dehydrogenation reaction, as compared to metal catalysts without the alumina over-coat.

ALD is a deposition technique in which vapors generated during each cycle can be sequentially directed to and/or sequentially contacted with a surface to form, for example, an alumina containing layer on the surface. The supported metal catalysts can be commercially purchased or formed with ALD. Forming supported metal catalysts with ALD is discussed in U.S. Provisional Application Ser. No. 61/276,260, titled "METAL CONTAINING COMPOSITES", The Dow Chemical Company, the disclosure which is incorporated herein by reference.

Supported metal catalysts include a substrate which supports a support, e.g., an oxide support, and metal particles that are chemically bonded to the support. Metal particles provide an activation site for the catalytic reaction.

Examples of the metal particles of the supported metal catalysts include, but are not limited to, palladium, platinum, rhodium, iridium, ruthenium, rhenium, gold, silver, copper, nickel, and combinations thereof. The metal particle is preferably palladium.

Examples of the support include, but are not limited to, aluminum oxide, titanium dioxide, silicon dioxide, niobium oxide, copper oxide, iron oxide, zinc oxide, cerium oxide, magnesium oxide, zirconium oxide, carbon aerogel, and combinations thereof. The support is preferably aluminum oxide. Additionally, the support of the supported metal catalyst can be porous or can be non-porous.

The substrate can have the same chemical composition or different chemical composition as the support. Examples of the substrate include, but are not limited to, silicon, glass, metals, polymers, porous host matrices (aerogels, silica gel, mesoporous silica), nitride, sulfide, carbon, nanowires, oxides, and combinations thereof.

The alumina over-coat is formed of sequential layers of the ligand-containing alumina precursors (also referred herein as "alumina precursors") and oxidizing reagents deposited via ALD. The deposition of each of the layers provides a consistently uniform layer growth rate for the alumina over-coat. There is an essentially constant growth rate of the alumina over-coat for each of the ALD cycles used in forming the alumina over-coat such that the thickness of the alumina over-coat is controlled to the atomic level.

ALD is performed in a viscous flow reactor system as discussed in J. W. Elam, M. D. Groner and S. M. George, "Viscous Flow Reactor with Quartz Crystal Microbalance for Thin Film Growth by Atomic Layer Deposition", Rev. Sci. Instrum. 73, 2981-2987 (2002), which is herein incorporated by reference. Other ALD systems are also suitable for embodiments of this disclosure. The ALD system maintains a temperature within a range of from 20° C. to 600° C.

The alumina over-coat can be formed on the supported metal catalyst by ALD, as described herein. For ALD, vapors used to form the alumina over-coat are sequentially pulsed into a reactor of the ALD system. "Vapors" include volatile and/or high vapor pressure liquids and/or solids.

Each ALD cycle of the present disclosure includes the following steps. An ALD cycle includes contacting a supported metal catalyst surface with a ligand-containing alumina precursor for a predetermined contact time to form an intermediate layer having a plurality of aluminum moieties that chemically bond to the supported metal catalyst surface. The predetermined contact time is from 1 second (s) to 300 s, preferably 60 s. Ligand-containing alumina precursors are selected from compounds having the formula $Al(R^1)_3$, where each $R^1$ is independently methyl, ethyl, propyl, chloride, bromide, dialkylamino, or alkoxide.

The ALD cycle includes contacting the intermediate layer with an inert gas for a predetermined intermediate stripping time to remove unreacted ligand-containing alumina precursors. The predetermined intermediate stripping time is from 1 s to 300 s, preferably 60 s. The inert gas is selected from the group consisting of helium, nitrogen, argon, neon, carbon dioxide and a combination thereof.

The ALD cycle includes reacting the aluminum moieties with an oxidation reagent for a predetermined reaction time to convert at least a portion of the ligands to hydroxyl groups thereby forming a layer of the alumina over-coat on the supported metal catalyst surface or a previously formed layer of the alumina over-coat. The predetermined reaction time is from 1 s to 300 s, preferably 60 s. Oxidizing reagents are selected from the group including water, ethylene glycol, formalin, ammonia, hydrogen sulfide, hydrogen peroxide, nitrous oxide, nitrogen dioxide, phosphine, arsine, and combinations thereof.

Prior to forming an additional layer of the alumina over-coat, the ALD cycle includes contacting the layer of the alumina over-coat previously formed with an inert gas for a predetermined final stripping time to remove unreacted oxidation reagents. The predetermined final stripping time is from 1 s to 300 s, preferably 60 s.

The predetermined times discussed herein are not limited to the ranges provided and other predetermined times are possible.

Each ALD cycle can be performed two or more times. Different numbers of ALD cycles can be performed to obtain an optimal thickness for various applications. While a number of ALD cycles can be performed, the accessibility of the metal particles of the supported metal catalyst may contribute to determining the number of ALD cycles for particular applications. For example, if the thickness of the alumina over-coat is too small (e.g., less than 1 nm) the alumina over-coat may not minimize coking and sintering. On the other hand, if the thickness of the alumina over-coat is too large (e.g., greater than 15 nm) the metal particles may not be accessible by the reactants during the dehydrogenation or oxidative dehydrogenation reactions; thereby rendering the catalyst ineffective.

A thickness of the over-coat is dependent on the number of ALD cycles that deposited the over-coat and is controlled to the nanometer. The alumina over-coat has a thickness from 1 nm to 100 nm, preferably 1 nm to 15 nm, more preferably 9 nm.

The method includes activating the alumina over-coat. Activating forms pores in the alumina over-coat allowing the metal particles to become accessible by the reactants. During activation, the alumina over-coat undergoes a structural transformation from the surface of the alumina over-coat to the metal particles, and removes carbon residual that accumulated from the ALD process, which forms the pores and exposes the metal particle.

At least 80% of the pores in the alumina over-coat have a diameter within a range of from 0.3 to 5 nm, preferably within a range of from 0.5 nm to 3 nm. In some embodiments, at least 90% of the pores in the alumina over-coat have a diameter within a range of from 0.3 nm to 5 nm, preferably within a range of from 0.5 nm to 3 nm. The small diameter minimizes an amount of produced olefins that can reach the metal particles and helps to prevent coke formation.

Activating includes calcining and/or reducing. Calcining, also referred to as calcination, is the heating of a solid to a temperature below its melting point that brings about a thermal decomposition and/or dissociation. Calcining can occur in the presence of a non-reducing gas at a temperature within a range of from 30° C. to 1000° C. for a time interval within a range from 3 min to 5 days (i.e., 120 hours (hrs)). For some applications, calcining occurs at a temperature within a range of from 500° C. to 800° C. for 60 min to 10 hrs, and more preferably at 700° C. for 2 hrs. Suitable non-reducing gases include, but are not limited to, helium, nitrogen, argon, neon, oxygen, ozone, dry air, and combinations thereof. Calcining can be performed in the ALD system or in a separate reactor, where the separate reactor produces and maintains the calcination conditions as discussed herein.

Reduction can occur in the presence of hydrogen, hydrocarbons, carbon monoxide, formalin, and combinations thereof. Reduction can occur in the presence of a non-oxidizing gas at a temperature within a range of from 30° C. to 1000° C. for a time interval within a range from 3 min to 5 days. For some applications, reduction occurs at a temperature within a range of from 500° C. to 800° C. for 60 min to 10 hrs, and more preferably at 700° C. for 2 hrs. Suitable non-oxidizing gases include helium, nitrogen, argon, neon, hydrogen, and combinations thereof.

A method for reducing coke formation during dehydrogenation or oxidative dehydrogenation is disclosed. The method includes contacting an alkane with the metal catalyst composition in the presence of inert gas, oxygen, and combinations thereof at a temperature within a range of 300° C. to 800° C., where the metal catalyst composition is formed by performing a plurality of ALD cycles on a supported metal catalyst surface, as described herein. The alkanes can include, but are not limited to, C2 to C20 carbon atom alkanes, either alone or in mixtures, preferably having two to eight carbon atoms. Suitable alkanes include, but are not limited to, ethane, propane, n-butane isobutane, n-pentane, isoamylenes, n-hexane, isohexanes, n-heptane, isoheptane, octane and isooctanes. The alkanes may include both linear and branched alkanes.

Problems that lead to coking include the migration of metal particles and produced olefins polymerizing on the metal particle. It is believed that the alumina over-coat inhibits the problems that lead to coking. For example, the over-coat acts as a barrier such that the migration of the metal particles is inhibited. Since larger metal particles are more likely to make coke than small metal particles, minimizing the growth of metal particles, by preventing migration, helps minimize coke formation. Additionally, the alumina over-coat restricts the access of the produced olefins to the metal particles. By having pores with a diameter of 2 nm or less, the access of produced olefins is restricted to the metal particle and prevents the required concentration of produced olefins needed to polymerize from collecting on the metal particle.

EXAMPLES

Materials include trimethylaluminum (TMA), $(CH_3)_3Al$, assay 97%, Sigma-Aldrich®; palladium on alumina ($Pd/Al_2O_3$) catalyst, Pd nanoparticles with an average size of 3.2±0.67 nm and loading of 1.88%, synthesized by wet impregnation onto gamma $Al_2O_3$; formalin (37% HCOH and 15% $CH_3OH$ in aqueous solution), Sigma-Aldrich®; ultrapure water (Millipore™); palladium(II) hexafluoroacetylacetonate, $Pd(C_5HF_6O_2)_2$, (Sigma-Aldrich®); silica gel S10040M, (SiliCycle®); inert gas: nitrogen; Palladium nitrate ($Pd(NO_3)_2$), 10% solution, Johnson Matthey®; Citric acid; Gamma-alumina (180 $m^2/g$, 0.6 cc/g), Sasol®.

Equipment includes viscous flow reactor system (J. W. Elam and as discussed herein); mount quartz crystal microbalance (Maxtek Inc.), having thickness monitor model TM-400R and QCM sensors CCAT1-1007-000 (Colorado Crystal Corporation), in Maxtek BSH-150 bakeable sensor (INFICON) housing and seal with Epotek P1011 epoxy (Epoxy Technology, Inc.). Operate the reactor at a pressure of 1-2 Torr with the nitrogen flow at 360 standard cubic centimeters per minute (sccm). Monitor pressure by a 10 Torr Baratron capacitance manometer to maintain flow velocity of 2.5 meters/second. High resolution transmission electron microscope (TEM), (JEOL® JEM-2100F FAST TEM); Thermal gravimetric analysis (TGA), (TA Instrument); Diffuse reflectance Infrared (IR) spectroscopy (DRIFTS), (Thermo Nicolet Nexus 870 Instrument® with an MCT detector), and Nitrogen BET (ASAP 2020, Micromeritics®).

Ex 1

$45Al/Pd/Al_2O_3$

Figure 1:
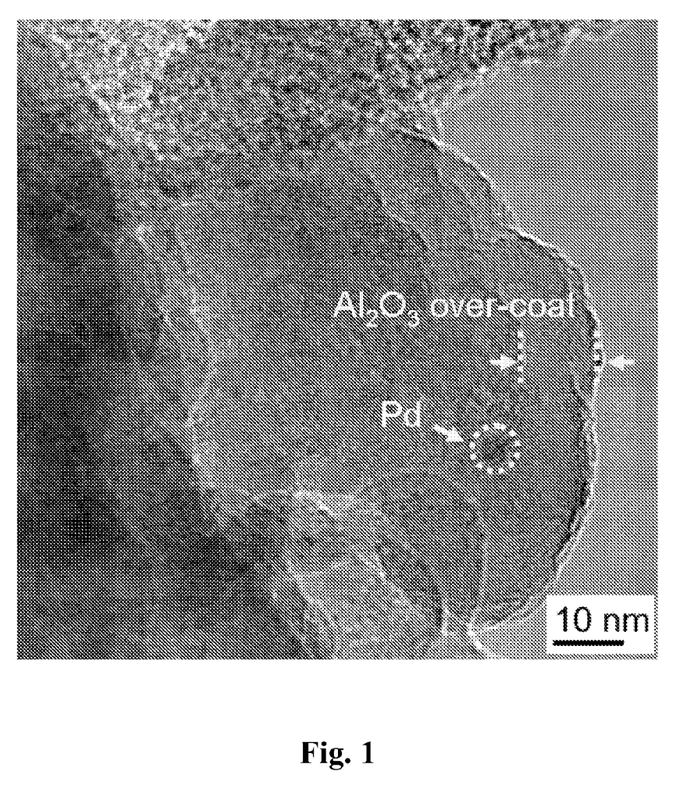
FIG. 1 illustrates a high resolution transmission electron microscope (TEM) image of the metal catalyst composition Example (Ex) 1.

Sequentially expose the $Pd/Al_2O_3$ catalyst to 45 ALD cycles including TMA and ultrapure water at 200° C. Each ALD cycle includes a 60 s TMA exposure, and a 60 s ultrapure water exposure, follow each exposure by a 60 s inert gas purge with nitrogen. The resulting as-prepared metal catalyst composition has a loading of 1.03%. TEM measurements showed that there is an approximately 9 nm alumina over-coat on the surface of the $Pd/Al_2O_3$ catalyst after the 45 ALD cycles, as seen in FIG. 1.

Activate the alumina over-coat by calcining the as-prepared metal catalyst composition at 700° C. for 2 hrs in 10% oxygen in helium and then reducing in 5% hydrogen in helium at 300° C. for 30 min.

Ex 2

$45Al/Pd/Al_2O_3$-ALD

Synthesize a $Pd/Al_2O_3$ catalyst by ALD using $Pd(C_5HF_6O_2)$ and formalin at 80° C. for one ALD cycle. The particle size of the Pd nanoparticles was 1.1±0.5 nm and has a loading of 0.41%. Sequentially expose the synthesized $Pd/Al_2O_3$ catalyst to 45 ALD cycles as described in Ex 1. The resulting as-prepared metal catalyst composition has a loading of 0.23%.

Activate the alumina over-coat by calcining the as-prepared metal catalyst composition at 700° C. for 2 hrs in 10% oxygen in helium and then reducing in 5% hydrogen in helium at 300° C. for 30 min.

Ex 3

$30Al/Pd/Al_2O_3$-ALD

Repeat Ex 2, but with changes. Perform 30 ALD cycles instead of 45 cycles.

Com Ex 1

$Pd/Al_2O_3$

Dissolve 3.0 g of citric acid in 2 mL water. Add 7 mL of 10% $Pd(NO_3)_2$ solution to the citric acid to form a Pd-citric acid solution. The Pd-citric acid solution was added drop wise to 15 g of gamma-alumina and dried for 1 hr at approximately 20° C. and then overnight at 125° C. to form the catalyst. Calcine 5 g of catalyst in flowing air at 300° C. for 5 hrs. Reduce the calcined catalyst in flowing hydrogen (200 sccm/min) by heating to 100° C. for 30 min then increasing the temperature to 175° C. for 30 min and finally 250° C. for 30 min, purge with He and cool to approximately 20° C.

Com Ex 2

$Pd/Al_2O_3$-ALD

Synthesize a $Pd/Al_2O_3$ catalyst by ALD using $Pd(C_5HF_6O_2)$ and formalin at 80° C. for one ALD cycle.

Accessibility of Ex 1 (45Al/Pd/$Al_2O_3$) at 200° C.

Figure 2:
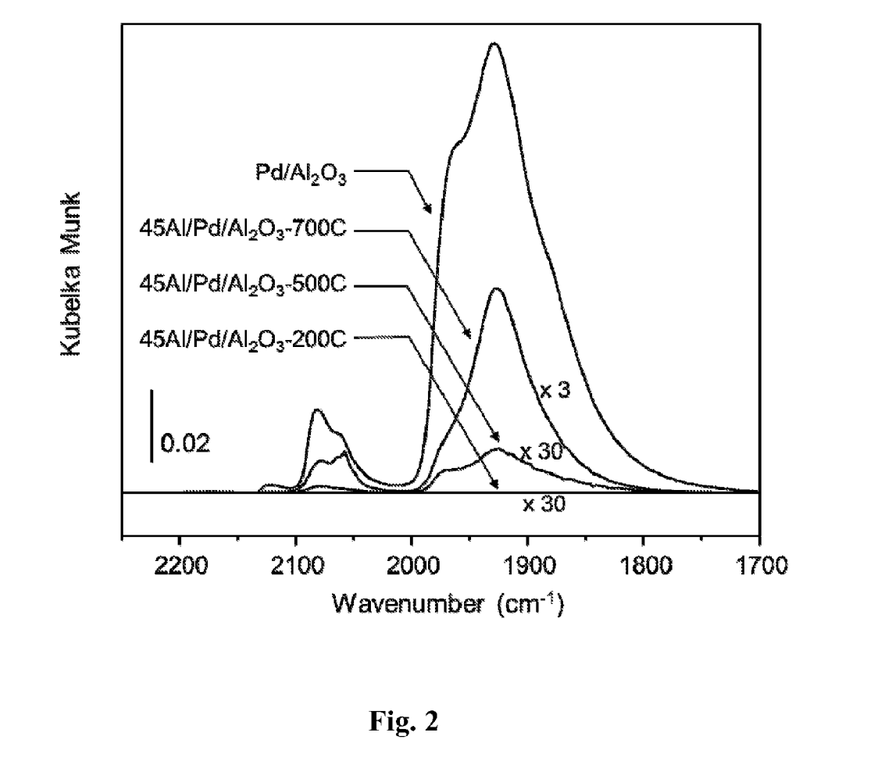
FIG. 2 illustrates diffuse reflectance infrared spectroscopy (DRIFTS) spectra of carbon monoxide (CO) chemisorption at saturation coverage on the metal catalyst composition of Ex 1 treated at different temperatures and of the uncoated metal catalyst of Comparative Example (Com Ex) 1.

Determine the accessibility of the as-prepared 45Al/Pd/$Al_2O_3$ from Ex 1 using DRIFTS with CO as a probe molecule after reducing in 5% hydrogen at 200° C. for 30 min. DRIFTS measurements of CO chemisorption were performed at 20° C. using a Thermo Nicolet Nexus 870 instrument with an MCT detector. A cold trap at approximately negative (−) 80° C. was used in the gas inlet line to remove all the iron carbonyls. The background spectra was taken after purging the sample with ultrahigh purity (99.999%) helium for 30 min at a flow rate of approximately 80 sccm. Pure CO (Airgas, research grade) at a flow rate of approximately 40 sccm was then introduced to the DRFITS cell for 20 min to saturate the Pd surface. After the CO saturation, another 5 min of helium purge at a flow rate of approximately 70 sccm was performed to remove gas phase CO in the DRIFTS cell. The spectrum was recorded (512 scans, a resolution of 4 $cm^{-1}$) after the helium purge.) The DRIFT spectra of CO chemsorption for 45Al/Pd/$Al_2O_3$-200° C. at saturation coverage is shown in FIG. 2.

Accessibility of Ex 1 (45Al/Pd/$Al_2O_3$) at 500° C.

Activate the alumina over-coat by calcining the as-prepared 45Al/Pd/$Al_2O_3$ from Ex 1 at 500° C. for 2 hrs in 10% oxygen in helium and then reduce in 5% hydrogen in helium at 300° C. for 30 min. Repeat the accessibility of Ex 1 (45Al/Pd/$Al_2O_3$) at 200° C. with changes. The Ex 1 (45Al/Pd/$Al_2O_3$) at 500° C. replaces the metal catalyst composition from of Ex 1 (45Al/Pd/$Al_2O_3$) at 200° C. The DRIFT spectra of CO chemsorption for 45Al/Pd/$Al_2O_3$-500° C. at saturation coverage is shown in FIG. 2.

Accessibility of Ex 1 (45Al/Pd/$Al_2O_3$) at 700° C.

Activate the alumina over-coat by calcining the 45Al/Pd/$Al_2O_3$ from Ex 1 at 700° C. for 2 hrs in 10% oxygen in helium and then reduce in 5% hydrogen in helium at 300° C. for 30 min. Then repeat Accessibility of Ex 1 (45Al/Pd/$Al_2O_3$) at 200° C. with changes. The Ex 1 (45Al/Pd/$Al_2O_3$) at 700° C. replaces the metal catalyst composition from of Ex 1 (45Al/Pd/$Al_2O_3$) at 200° C. The DRIFT spectra of CO chemsorption for 45Al/Pd/$Al_2O_3$-700° C. at saturation coverage is shown in FIG. 2.

Accessibility of Com Ex 1 (Pd/$Al_2O_3$)

Determine the accessibility of the uncoated metal catalyst of Com Ex 1. Repeat Accessibility of Ex 1 (45Al/Pd/$Al_2O_3$) at 200° C. with changes. The uncoated metal catalyst of Com Ex 1 replaces the metal catalyst composition from of Ex 1 (45Al/Pd/$Al_2O_3$) at 200° C. The DRIFT spectra of CO chemsorption for Pd/$Al_2O_3$ at saturation coverage is shown in FIG. 2.

Accessibility Analysis

As seen in FIG. 2, the results indicate that the 45Al/Pd/$Al_2O_3$-200° C. catalyst was completely covered by the alumina over-coat, thereby, minimizing the accessibility of the CO molecule. The results for the 45Al/Pd/$Al_2O_3$-500° C. and 45Al/Pd/$Al_2O_3$-700° C. indicate that as the temperature during calcining increases, the accessibility of the CO molecule also increases. The capacity of the CO peak of 45Al/Pd/$Al_2O_3$-700° C. is in the same order of the uncoated sample Pd/$Al_2O_3$, indicating that the alumina over-coat became porous to allow Pd nanoparticles to become reaccessible after the calincation treatments.

Reduction of Coke Formation: Using Ex 1 (45Al/Pd/$Al_2O_3$)

Figure 3:
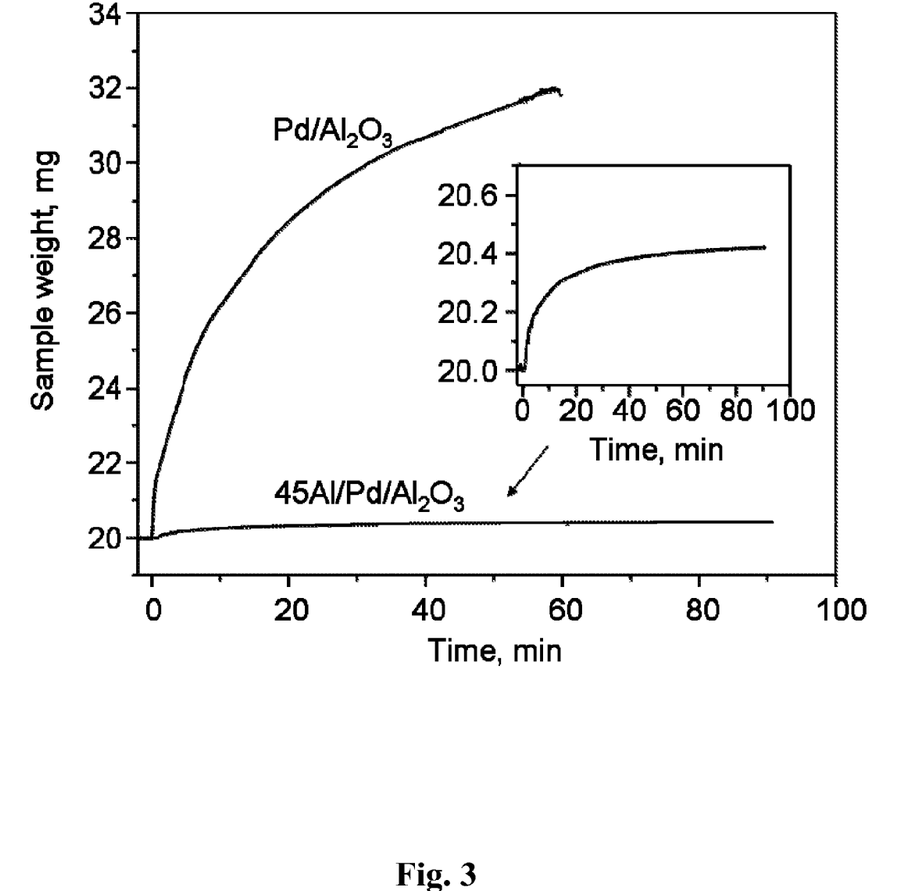
FIG. 3 illustrates thermal gravimetric analysis (TGA) measurements of coke formation on the metal catalyst composition of Ex 1 and on the uncoated metal catalyst of Com Ex 1.

Perform in situ TGA to quantify the reduction of coke formation using 20 milligrams (mg) of the metal catalyst composition from Ex 1 during an oxidative dehydrogenation of ethane (ODHE) reaction at 650° C. for 90 min. The flow rates of ethane, oxygen, and diluent helium are 10.5, 3.5, and 66.5 sccm, respectively. Prior to ODHE reaction, the sample was heated with a heating rate of 5° C./min in 10% oxygen/helium (80 sccm) to 700° C. and then maintain isothermal for 2 hrs. Cool the sample to 650° C. in helium (80 sccm) and then maintain isothermal for 1 hr. After the treatment, the mixture of reactants was introduced to the sample for 90 min at 650° C. The result is illustrated in FIG. 3.

Comparative Coke Formation: Using Com Ex 1 (Pd/$Al_2O_3$)

Repeat Reduction of Coke Formation: Using Ex 1 with changes. The uncoated metal catalyst of Com Ex 1 replaces the metal catalyst composition from Ex 1. The result is illustrated in FIG. 3.

Analysis

As seen in FIG. 3, the TGA results illustrate that there was 11.83 mg of coke formation on the 20 mg uncoated metal catalyst of Com Ex 1 after 60 min of the reaction at 650° C. For the metal catalyst composition of Ex 1, there was 0.40 mg of coke formation on the 20 mg metal catalyst composition of Ex 1 after 1 hr of the reaction at 650° C. The amount of coke formation on the metal catalyst composition from Ex 1 after 60 min was approximately 6.2% of the coke formation on the uncoated catalyst of Corn Ex 1. The amount of coke formation on the metal catalyst composition of Ex 1 slowly increased during the reaction period of 90 minutes but is still significantly lower than the coke formation on the uncoated metal catalyst of Com Ex 1.

Reduction of Coke Formation: Using Ex 2 (45Al/Pd/$Al_2O_3$-ALD)

Figure 4:
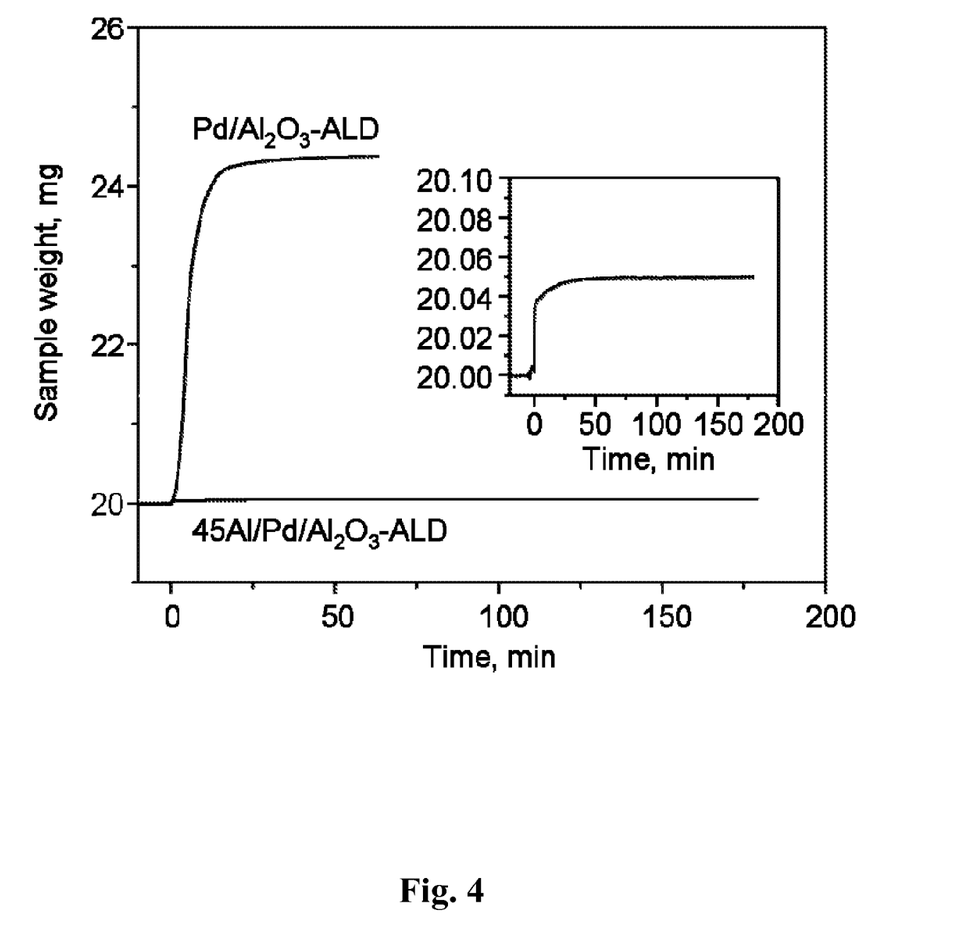
FIG. 4 illustrates TGA measurements of coke formation on the metal catalyst composition of Ex 2 and on the uncoated metal catalyst of Com Ex 2.

Repeat Reduction of Coke Formation: Using Ex 1 with changes. The metal catalyst composition from Ex 2 replaces the metal catalyst composition from Ex 1. The result is illustrated in FIG. 4.

Comparative Coke Formation 1: Using Com Ex 2 (Pd/$Al_2O_3$-ALD)

Repeat Reduction of Coke Formation: Using Ex 1 with changes. The uncoated metal catalyst of Com Ex 2 replaces the metal catalyst composition from Ex 1. The result is illustrated in FIG. 4.

Analysis

As seen in FIG. 4, the TGA results illustrate that there was 4.36 mg of coke formation on the 20 mg uncoated metal catalyst of Com Ex 2 after 1 hr of the reaction at 650° C. For the metal catalyst composition of Ex 2, there was 0.05 mg of coke formation on the 20 mg metal catalyst composition of Ex 1 after 1 hr of the reaction at 650° C. The amount of coke formation on the metal catalyst composition from Ex 2 was approximately 2.0% of the coke formation on the uncoated catalyst from Com Ex 2. The amount of coke formation on the metal catalyst composition of Ex 2 slowly increased during the reaction period of 180 minutes but is still significantly lower than the coke formation on the uncoated metal catalyst of Com Ex 2.

Thermal Stability: Using Ex 1 (45Al/Pd/$Al_2O_3$)

Dilute the as-prepared metal catalyst composition of Ex 1 with fine quartz chips and slowly heat up with a heating rate of 2° C./min. Calcine in 10% oxygen at 700° C. for 2 hrs.

Perform an oxidative dehydrogenation of ethane (ODHE) at 675° C. for 28 hrs. The flow rates of ethane, oxygen, and diluent helium are 9, 3, and 48 sccm, respectively. Use STEM measurements to determine any morphology changes of the Pd nanoparticles. No visible morphology changes of the Pd nanoparticles were observed on the used catalyst.

Thermal Stability: Using Ex 2 (45Al/Pd/Al$_2$O$_3$-ALD)

Repeat Thermal Stability: Using Ex 1 with changes. The metal catalyst composition of Ex 2 replaces the metal catalyst composition of Ex 1. No visible morphology changes of the Pd nanoparticles were observed on the used catalyst.

Thermal Stability: Using Ex 3 (30 Al/Pd/Al$_2$O$_3$-ALD)

Figure 5:
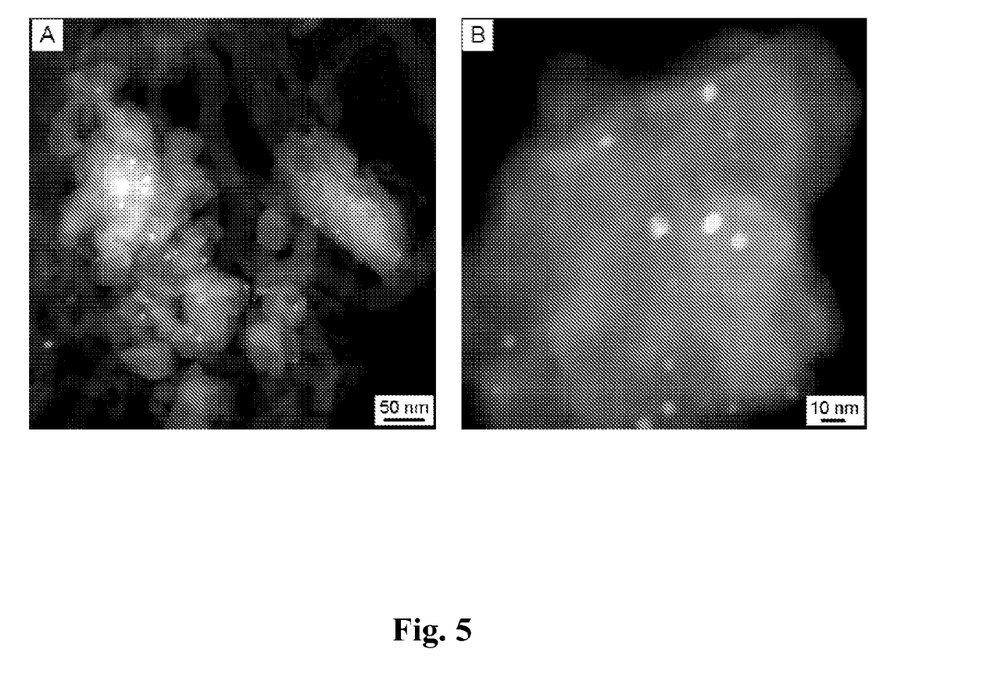
FIG. 5 illustrates scanning transmission electron microscopy (STEM) images for the over-coated catalyst of Ex 3.

Repeat Thermal Stability: Using Ex 1 with changes. The metal catalyst composition of Ex 3 replaces the metal catalyst composition of Ex 1. The results are illustrated in Table 1 and the STEM images are shown in FIG. 5. Considerable morphology changes were observed, the STEM images are shown in FIG. 5.

As seen in FIG. 5, (A) illustrates the 30Al/Pd/Al$_2$O$_3$-ALD catalyst after the ODHE reaction with low magnification and (B) illustrates the 30Al/Pd/Al$_2$O$_3$-ALD catalyst after the ODHE reaction with high magnification.

Thermal Stability: Using Com Ex 1 (Pd/Al$_2$O$_3$)

Repeat Thermal Stability: Using Ex 1 with changes. The uncoated metal catalyst of Com Ex 1 replaces the metal catalyst composition of Ex 1 and the ODHE reaction was run for 30 min because the coke formation blocked the reactor and shut down the reaction. STEM measurements demonstrated that there was nanowire formation and considerable sintering on the used catalyst. The STEM images are shown in FIG. 6.

Figure 6:
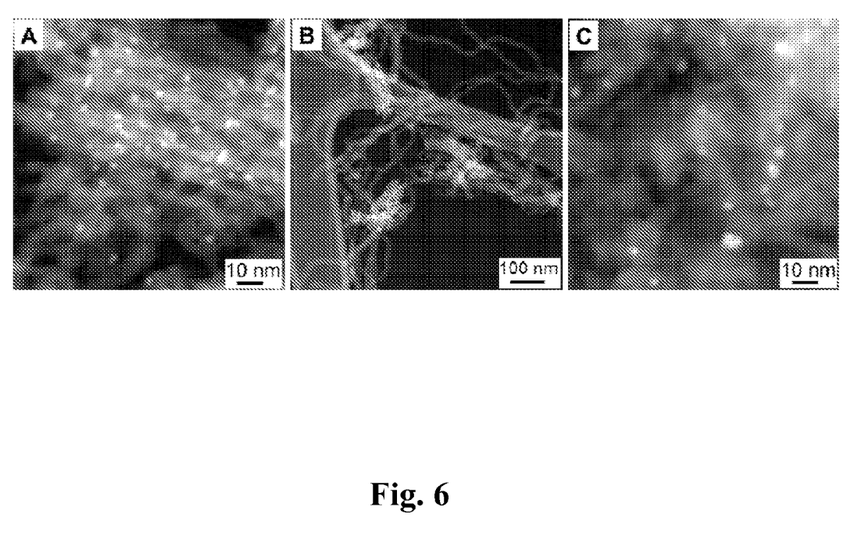
FIG. 6 illustrates STEM images for the uncoated catalyst in Com Ex 1.

As seen in FIG. 6, (A) illustrates fresh unused Pd/Al$_2$O$_3$ catalyst and (B) and (C) illustrate the used Pd/Al$_2$O$_3$ catalyst after the ODHE reaction with different magnification.

Thermal Stability: Using Com Ex 2 (Pd/Al$_2$O$_3$-ALD)

Repeat Thermal Stability: Using Ex 1 with changes. The uncoated metal catalyst of Com Ex 2 replaces the metal catalyst composition of Ex 1 and the ODHE reaction was run for 30 min because of the coke formation. STEM measurements demonstrated that there was nanowire formation and considerable sintering on the used catalyst. The STEM images are shown in FIG. 7.

Figure 7:
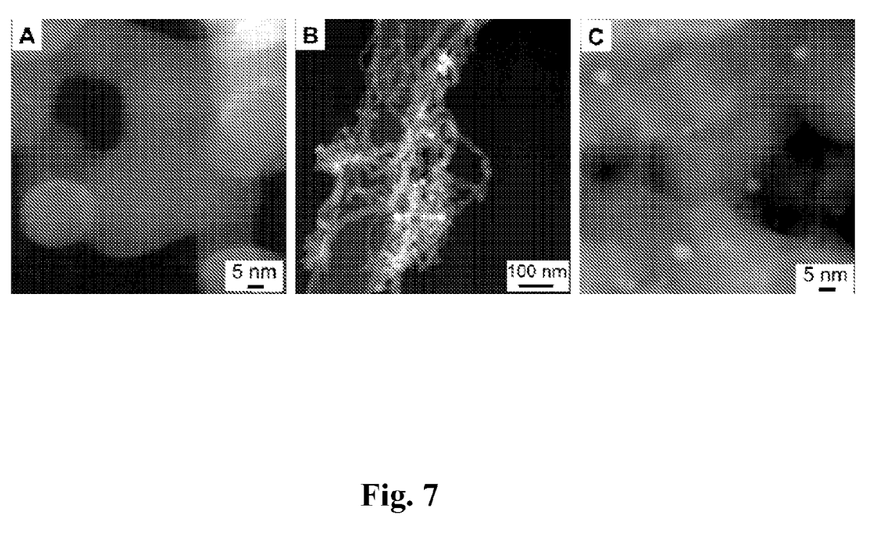
FIG. 7 illustrates STEM images for the uncoated catalyst in Com Ex 2.

As seen in FIG. 7, (A) illustrates fresh unused Pd/Al$_2$O$_3$-ALD catalyst and (B) and (C) illustrate the used Pd/Al$_2$O$_3$-ALD catalyst after the ODHE reaction with different magnification.

Dehydrogenation of Ethane (DHE): Using Ex 2 (45Al/Al$_2$O$_3$-ALD)

Figure 8:
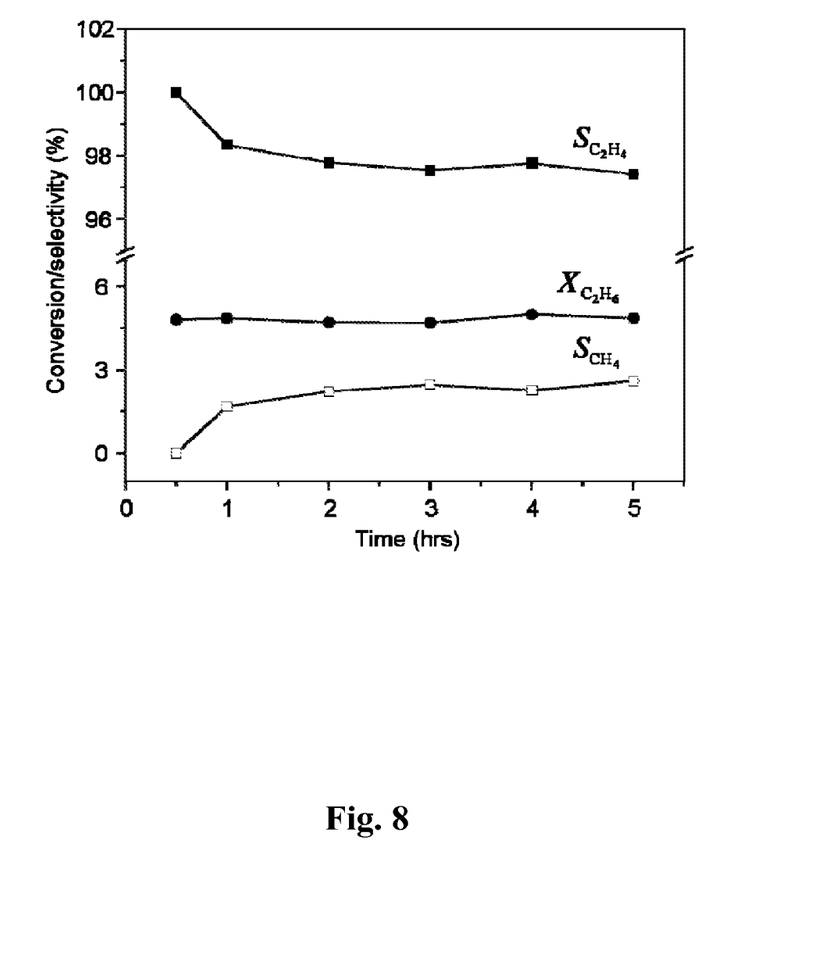
FIG. 8 illustrates the dehydrogenation of ethane (DHE) reaction test using the metal catalyst composition of Ex 2.

Perform a DHE reaction with the metal catalyst composition at 675° C. for 5 hrs with a flow of ethane at 9 sccm and N$_2$ at 41 sccm. The conversion of ethane was found to be 4.9%, with an ethylene selectivity of 97.6%, which is shown in FIG. 8. There was no visible decrease in activity in the period of 5 hrs during the DHE reaction and the selectivity of ethylene only slightly dropped from 1% to 97.6% after 2 hrs. This long term of DHE reaction test suggests that the metal catalyst compositions inhibit coke formation in DHE reactions, as compared to reaction using catalysts that do not have the over-coat normally deactivate in a few minutes due to large coke deposition.

Porosity of ALD Applied Over-Coat

Use silicycle S10040M SiO$_2$ having a surface area of approximately 100 meters squared per gram (m$^2$/g), a primary particle size of 75-200 micrometers (µm) as a support. Load 500 mg of the support onto a powder holder and hold in the ALD system at 200° C. Sequentially expose the support to TMA and ultrapure water at 200° C. for 45 ALD cycles. Each ALD cycle includes a 60 s TMA exposure, and a 60 s ultrapure water exposure, and follow each exposure by a 60 s inert gas purge with nitrogen. Use nitrogen BET to determine the pore size distribution of the alumina over-coat as-prepared and after calcination at 700° C. in air for 2 hrs. The results are shown in FIG. 9.

Figure 9:
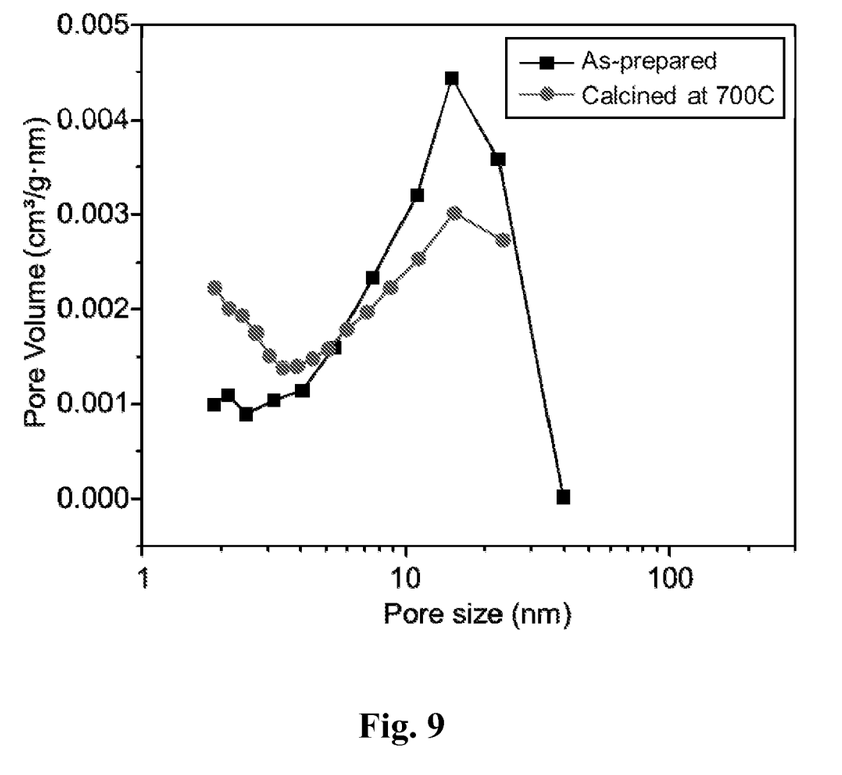
FIG. 9 illustrates the pore size distribution of the metal catalyst composition of Ex 1 before and after activation.

As seen in FIG. 9, the pore size distribution of the as-prepared over-coated support and the over-coated support after calcinations illustrate that the population of the pores at the size of approximately 2 nm significantly increased after high temperature treatment, which was evidentially identical to the size of the pores formed on the 45Al/Pd/Al$_2$O$_3$ catalysts after the same treatment. Therefore the formation of the pores within the ALD Al$_2$O$_3$ over-coats is most likely due to removal of carbon residues from the ALD process. Certainly, the structural changes in the amorphous Al$_2$O$_3$ over-coats could also contribute the pore formation by the thermal treatment.

Porosity of Over-Coated Metal Catalyst: Using Ex 1 (45Al/Pd/Al$_2$O$_3$)

Figure 10:
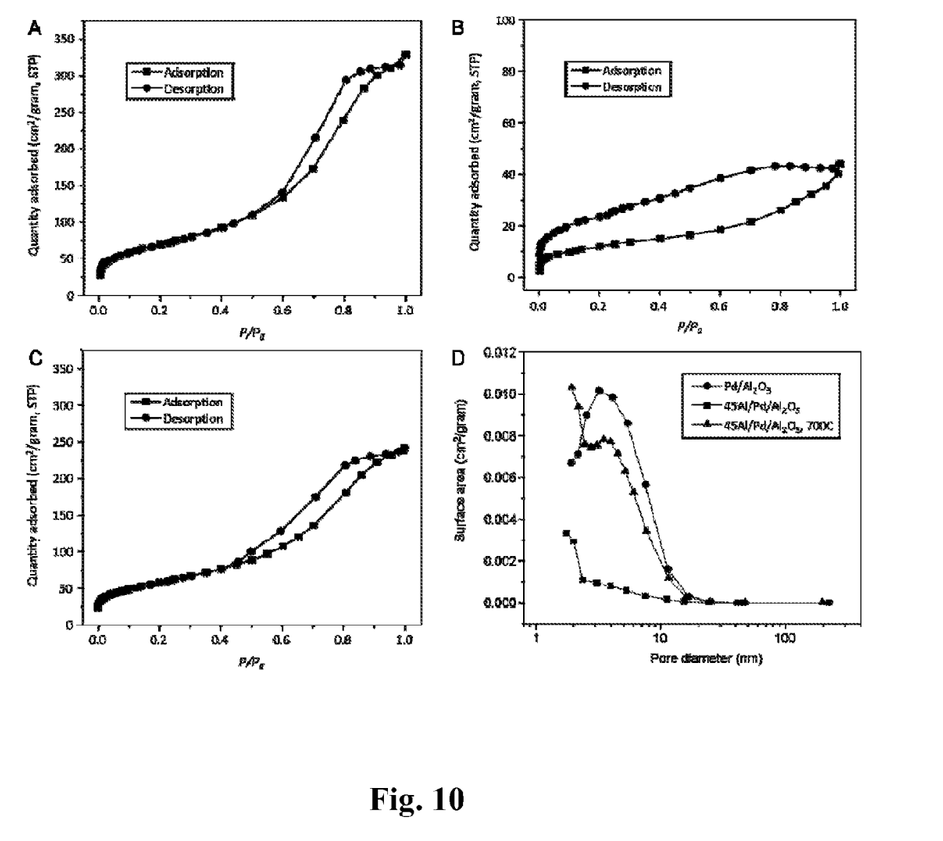
FIG. 10A illustrates the nitrogen adsorption-desorption isotherms of the uncoated metal catalyst of Com Ex 1.
FIG. 10B illustrates the nitrogen adsorption-desorption isotherms of the metal catalyst composition of Ex 1 prior to activation.
FIG. 10C illustrates the nitrogen adsorption-desorption isotherms of the metal catalyst composition of Ex 1 after activation.
FIG. 10D illustrates the pore size distribution calculated from the adsorption branch of the isotherms for FIG. 10A-C.

Determine the porosity of the alumina over-coat by nitrogen BET. In order to address the changes in surface area and pore size distribution, the quantity of adsorbed nitrogen and surface area were normalized based on the weight of an uncoated catalyst (Pd/Al$_2$O$_3$). The BET surface area, as deduced from the adsorption-desorption isotherms of the uncoated catalyst (Pd/Al$_2$O$_3$), the as-prepared metal catalyst composition of Ex 1, and the metal catalyst composition of Ex 1 after activating the over-coat are shown in FIGS. 10A, 10B, and 10C, respectively. As seen in FIGS. 10A and 10B, the surface area decreased from 253 m$^2$/gram to 30 m$^2$/gram as a consequence of applying 45 ALD cycles. The large hysteresis loop observed in FIG. 10B indicates that slit-shaped pores were formed after the ALD cycles.

However, after activating the alumina over-coat by calcining at 700° C. for 2 hr under 10% oxygen in helium followed by reduction under 5% hydrogen in helium at 300° C. for 30 min (45Al/Pd/Al$_2$O$_3$-700 C), the BET surface area returned to 213 m$^2$/gram, shown in FIG. 10C.

FIG. 10D illustrates the pore size distribution calculated from the absorption branch of the isotherms of the samples in FIGS. 10A-10C. FIG. 10D illustrates the Al$_2$O$_3$ support of the uncoated Pd/Al$_2$O$_3$ catalyst was mesoporous with an average pore size of 6.6 nm. After 45 cycles of ALD Al$_2$O$_3$ over-coating, the mesopores disappeared, revealing the dramatic BET surface area decrease. This is not surprising, since the thickness of ALD Al$_2$O$_3$ over-coat (approximately 9 nm, as shown in FIG. 1) is greater than the characteristic diameter of the mesopores. After high temperature treatment, the mesopores with a diameter of 6.6 nm were restored, and new pores were formed at approximately 2 nm (FIG. 10D). The pores were formed by structural changes in the amorphous Al$_2$O$_3$ over-coat caused by the thermal treatment, removal of carbon residues from the ALD process, and dewetting of the Al$_2$O$_3$ over-coat from the surface of the Pd nanoparticles caused by the large lattice mismatch between palladium and alumina. These pores made it possible for the embedded Pd nanoparticles to become accessible while the overlayer imparts high thermal stability.

What is claimed:

1. A method of forming a metal catalyst composition, comprising:
    performing a plurality of atomic layer deposition cycles to form metal oxide over-coat on a supported metal catalyst, where one or more of the atomic layer deposition cycles include sequential steps:

(a) contacting a supported metal catalyst surface with a ligand-containing metal oxide precursor for a predetermined contact time to form an intermediate layer having a plurality of metal moieties that chemically bond to the supported metal catalyst surface;

(b) reacting the metal moieties with water for a predetermined reaction time to convert at least a portion of the ligands to hydroxyl groups thereby forming a layer of the metal oxide, metal hydroxide, or metal oxyhydroxide over-coat on the supported metal catalyst surface or a previously formed layer of the metal oxide, metal hydroxide, or metal oxyhydroxide over-coat;

(c) prior to replicating sequential steps (a) and (b) to form an additional layer of the metal oxide over-coat, contacting the layer of the metal oxide, hydroxide, oxyhydroxide over-coat formed in step b) with an inert gas for a predetermined final stripping time to remove unreacted water; and (d) activating the metal oxide, metal hydroxide, metal oxyhydroxide over-coat, after forming a final layer of the said over-coat, in the presence of a non-reducing gas at a temperature within a range from 500° C. to 800° C. for 60 minutes to 10 hours to form a layer of metal oxide having a thickness of from 1 nanometer to 100 nanometers with a plurality of pores therein, where at least 80 percent of the plurality of pores have a diameter within a range of 0.3 nanometers to 5 nanometers, and where the metal catalyst composition reduces an amount of coke formed during a dehydrogenation or an oxidative dehydrogenation reaction, as compared to same supported metal catalysts without the metal oxide over-coat.

2. The method of claim 1, where the metal oxide is aluminum oxide.

3. The method of claim 1, where the ligand-containing metal oxide precursor is selected from the group consisting of $M(R^1)_3$, where M is the metal and where each $R^1$ is independently methyl, ethyl, propyl, chloride, bromide, dialkylamino, or alkoxide.

4. The method of claim 1, where the supported metal catalyst includes a support having metal particles.

5. The method of claim 1, where contacting the supported metal catalyst surface with the ligand-containing metal oxide precursor includes contacting the supported metal catalyst surface with a ligand-containing alumina precursor, and contacting the intermediate layer with an inert gas for a predetermined intermediate stripping time removes ligand-containing alumina precursors that did not react.

6. A metal catalyst composition, comprising:
a supported metal catalyst including a support having a plurality of metal particles; and
an alumina over-coat deposited on a surface of the supported metal catalyst by atomic layer deposition followed by activating the alumina over-coat by heating in the presence of a non-reducing gas at a temperature within a range from 500° C. to 800° C. for 60 minutes to 10 hours, where activating the alumina over-coat forms pores, where at least 80 percent of the pores have a diameter within a range of 0.3 nanometers to 5 nanometers, where the alumina over-coat has a thickness within a range of from 1 nanometer to 100 nanometers, and where the metal catalyst composition reduces an amount of coke formation during a dehydrogenation reaction, as compared to metal catalysts without the alumina over-coat.

7. The metal catalyst of claim 6, where the alumina over-coat has a thickness within a range of from 1 nanometer to 15 nanometers.

8. The metal catalyst of claim 6, where depositing alumina layers on the surface of the supported metal catalyst includes a plurality of atomic layer deposition cycles including a ligand-containing alumina precursor and an oxidizing reagent.

9. The metal catalyst of claim 6, where at least 80 percent of the pores in the alumina over-coat have a diameter within a range of from 0.5 nanometers to 3 nanometers.

10. The metal catalyst of claim 6, where the ligand-containing alumina precursor is trimethylaluminum and the oxidizing reagent is water.

11. A method for reducing coke formation during a dehydrogenation reaction, comprising:
contacting an alkane with a metal catalyst composition in the presence of inert gas, oxygen, and combinations thereof, and at a temperature within a range of 300 degrees Celsius to 800 degrees Celsius, where the metal catalyst composition is formed by performing a plurality of atomic layer deposition cycles to form an alumina over-coat on a supported metal catalyst, where one or more of the atomic layer deposition cycles include sequentially;
contacting a supported metal catalyst surface with a ligand-containing alumina precursor for a predetermined contact time to form an intermediate layer having a plurality of aluminum moieties that chemically bond to the supported metal catalyst surface;
contacting the intermediate layer with an inert gas for a predetermined intermediate stripping time to remove unreacted ligand-containing alumina precursors;
reacting the aluminum moieties with water for a predetermined reaction time to convert at least a portion of the ligands to hydroxyl groups thereby forming a layer of the alumina over-coat on the supported metal catalyst surface or a previously formed layer of the alumina over-coat;
contacting the layer of the alumina over-coat formed with an inert gas for a predetermined final stripping time to remove unreacted water; and
activating the alumina over-coat in the presence of a non-reducing gas at a temperature within a range from 500° C. to 800° C. for 60 minutes to 10 hours, after forming a final layer of the alumina over-coat having a thickness of from 1 nanometer to 100 nanometers, to form a plurality of pores in the alumina over-coat, where at least 80 percent of the plurality of pores have a diameter within a range of from 0.3 nm to 5 nanometers, and where the metal catalyst composition reduces an amount of coke formed during a dehydrogenation reaction or an oxidative dehydrogenation reaction, as compared to metal catalysts without the alumina over-coat.

\* \* \* \* \*